(12) United States Patent
Sawa et al.

(10) Patent No.: US 8,974,505 B2
(45) Date of Patent: Mar. 10, 2015

(54) VENTING/PRESSURE ADJUSTMENT TO AID IN DELIVERY OF MATERIAL INTO AN ANATOMIC REGION VIA A CANNULA

(76) Inventors: Anna G. U. Sawa, Phoenix, AZ (US); Seungwon Baek, Phoenix, AZ (US); Neil R. Crawford, Tempe, AZ (US); Phillip M. Reyes, Mesa, AZ (US); Sam Safavi-Abbasi, Oklahoma City, OK (US); Nicholas Theodore, Phoenix, AZ (US)

( * ) Notice: Subject to any disclaimer, the term of this patent is extended or adjusted under 35 U.S.C. 154(b) by 771 days.

(21) Appl. No.: 12/485,183

(22) Filed: Jun. 16, 2009

(65) Prior Publication Data

US 2010/0106199 A1 Apr. 29, 2010

Related U.S. Application Data

(60) Provisional application No. 61/132,041, filed on Jun. 16, 2008.

(51) Int. Cl.
*A61B 17/86* (2006.01)
*A61B 17/88* (2006.01)
*A61B 17/70* (2006.01)
*A61B 17/00* (2006.01)

(52) U.S. Cl.
CPC ............ *A61B 17/864* (2013.01); *A61B 17/7098* (2013.01); *A61B 17/8827* (2013.01); *A61B 17/7032* (2013.01); *A61B 2017/00544* (2013.01); *A61B 17/8685* (2013.01)
USPC ............................................. 606/304; 606/92

(58) Field of Classification Search
USPC ................. 606/65–67, 323, 92–94, 300–321; 411/82, 82.1, 257, 258, 381, 382, 395, 411/411, 422, 23, 403–405, 930
See application file for complete search history.

(56) References Cited

U.S. PATENT DOCUMENTS

| | | | | |
|---|---|---|---|---|
| 2,437,381 A | * | 3/1948 | Cullen | 27/21.1 |
| 3,579,831 A | * | 5/1971 | Stevens et al. | 433/174 |
| 4,712,957 A | * | 12/1987 | Edwards et al. | 411/82.1 |
| 5,464,427 A | * | 11/1995 | Curtis et al. | 606/232 |
| 5,478,342 A | * | 12/1995 | Kohrs | 606/310 |
| 5,584,836 A | * | 12/1996 | Ballintyn et al. | 606/232 |
| 5,725,581 A | * | 3/1998 | Brånemark | 606/304 |
| 5,735,898 A | * | 4/1998 | Brånemark | 623/11.11 |
| 5,827,285 A | * | 10/1998 | Bramlet | 606/60 |
| 5,849,004 A | * | 12/1998 | Bramlet | 606/232 |
| 6,048,343 A | * | 4/2000 | Mathis et al. | 606/916 |
| 6,168,598 B1 | * | 1/2001 | Martello | 606/74 |

(Continued)

*Primary Examiner* — Michael T Schaper
(74) *Attorney, Agent, or Firm* — Booth Udall Fuller, PLC

(57) ABSTRACT

A cannulated and possibly fenestrated device for injection of material into bone can be dangerous because large, uncontrolled pressures are introduced during injection into a somewhat closed system, and material may extrude undesirably or emboli may be introduced. Methods and devices are described for providing venting of pressure upon injection of material through cannulated and possibly fenestrated screws. The first method involves a bone screw and/or anchor device that includes multiple channels to allow material to flow in through one channel and out through another channel. The second method involves a plunger that can force material into bone if advanced or lessen pressure if withdrawn. The third method involves usage of two separate screws. Material is alternately injected or withdrawn from each screw to cause material to flow from one screw to the other in a controlled way that creates a uniform or asymmetrical distribution of material as desired.

3 Claims, 5 Drawing Sheets

(56) References Cited

U.S. PATENT DOCUMENTS

| | | | |
|---|---|---|---|
| 6,471,707 B1* | 10/2002 | Miller et al. | 606/916 |
| 6,517,542 B1* | 2/2003 | Papay et al. | 606/232 |
| 6,554,830 B1* | 4/2003 | Chappius | 606/246 |
| 6,558,388 B1* | 5/2003 | Bartsch et al. | 606/62 |
| 6,569,188 B2* | 5/2003 | Grafton et al. | 606/232 |
| 6,588,999 B2* | 7/2003 | Kubler et al. | 411/82.1 |
| 6,604,899 B2* | 8/2003 | Kubler et al. | 411/82 |
| 6,902,366 B2* | 6/2005 | Ducker et al. | 411/82.1 |
| 7,163,540 B2* | 1/2007 | Martello | 606/319 |
| 7,250,055 B1* | 7/2007 | Vanderwalle | 606/92 |
| 7,488,320 B2* | 2/2009 | Middleton | 606/62 |
| 7,713,285 B1* | 5/2010 | Stone et al. | 606/232 |
| 7,867,239 B2* | 1/2011 | Muhanna et al. | 606/104 |
| 8,267,981 B2* | 9/2012 | Boock et al. | 606/308 |
| 8,317,825 B2* | 11/2012 | Stone | 606/213 |
| 8,439,220 B2* | 5/2013 | Norman et al. | 220/367.1 |
| 8,556,558 B1* | 10/2013 | Hunt | 411/82.1 |
| 8,579,940 B2* | 11/2013 | Dreyfuss et al. | 606/232 |
| 8,617,226 B2* | 12/2013 | Kim | 606/310 |
| 2001/0007074 A1* | 7/2001 | Strobel et al. | 606/73 |
| 2002/0022840 A1* | 2/2002 | Martello | 606/60 |
| 2002/0032466 A1* | 3/2002 | Grafton et al. | 606/232 |
| 2003/0035696 A1* | 2/2003 | Ducker et al. | 411/82.1 |
| 2003/0083662 A1* | 5/2003 | Middleton | 606/72 |
| 2004/0033120 A1* | 2/2004 | Ducker et al. | 411/82.1 |
| 2004/0109738 A1* | 6/2004 | Ducker et al. | 411/82.1 |
| 2004/0230196 A1* | 11/2004 | Martello | 606/73 |
| 2004/0254580 A1* | 12/2004 | Boock et al. | 606/73 |
| 2005/0222619 A1* | 10/2005 | Dreyfuss et al. | 606/232 |
| 2006/0086214 A1* | 4/2006 | Smed | 81/461 |
| 2006/0111720 A1* | 5/2006 | Luca | 606/73 |
| 2006/0155286 A1* | 7/2006 | Wang | 606/73 |
| 2008/0012241 A1* | 1/2008 | Norman et al. | 277/616 |
| 2009/0204117 A1* | 8/2009 | Middleton | 606/62 |
| 2011/0015684 A1* | 1/2011 | Belcheva et al. | 606/314 |
| 2011/0097377 A1* | 4/2011 | Serhan et al. | 424/423 |
| 2011/0282418 A1* | 11/2011 | Saunders et al. | 607/105 |
| 2012/0053626 A1* | 3/2012 | Koepke | 606/232 |
| 2012/0221062 A1* | 8/2012 | Wenger et al. | 606/304 |
| 2013/0030478 A1* | 1/2013 | Rodriguez | 606/323 |
| 2014/0058461 A1* | 2/2014 | Black | 606/314 |

* cited by examiner

VENTING/PRESSURE ADJUSTMENT TO AID IN DELIVERY OF MATERIAL INTO AN ANATOMIC REGION VIA A CANNULA

RELATED US APPLICATION DATA

This application claims benefit under 35 U.S.C. §119(e) of U.S. provisional patent application Ser. No. 61/132,041 filed on Jun. 16, 2008.

FIELD OF THE INVENTION

This invention generally relates to the medical use of screws or tubes anchored in bone or soft tissues, and particularly, to methods and systems for controlling the pressure of material delivered through the cannulations or fenestrations in the screws or tubes by venting.

BACKGROUND OF THE INVENTION

During certain medical procedures such as vertebroplasty, bone screw augmentation, or drug-delivery, it is desirable to inject foreign materials (cements, medications, etc.) into bone or other anatomic regions. For example, delivery of materials through screws with a single cannulation that may or may not include slots (fenestrations) is described in U.S. Pat. No. 6,214,012 B1, "METHOD AND APPARATUS FOR DELIVERING MATERIAL TO A DESIRED LOCATION." However, local changes and increases in pressure at the regional injection sites can make injection through a single cannula or a radially fenestrated cannula difficult (requiring high pressures) and dangerous (can cause fat embolisms and hypertension). Apparatuses and methods that allow for venting/pressure adjustment of the injection site or region close to the delivery site are presented here, representing an improvement to this previous patent.

SUMMARY OF INVENTION

This application includes three related methods/devices for providing the venting of pressure upon injection of material through cannulated and/or fenestrated screws or tubes. The first method involves a device for insertion into bone or other tissue that includes at least two channels (e.g., hollow pathways, tunnels, cannulations), where one channel provides a pathway for material going into the bone/anatomic region and a second/additional channel provides a pathway for material (body fluids) going out of the bone/anatomic region near the site to be injected. The second method involves a plunger that can force material into bone if the plunger is advanced or lessen pressure if the plunger is withdrawn. The third method involves usage of two separate screws, each with a single cannulation. Material is alternately injected or withdrawn from each screw or tube to cause material to flow from one screw or tube to the other and vice versa in a controlled way that can create a uniform or asymmetrical distribution of material as desired.

BRIEF DESCRIPTION OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

The first of the three related methods involves a bone screw and/or anchor device that includes at least two channels (e.g., hollow pathways, tunnels, cannulations), where one channel provides a pathway for material going into the bone/anatomic region and a second/additional channel provides a pathway for material (body fluids) going out of the bone/anatomic region near the site to be injected.

The delivery and removal sites are close enough to each other so that the pressure at one site affects the other; that is, removal of material/fluid from the removal site should reduce the pressure at the delivery site, while injection of a material at the delivery site should increase the pressure at the removal side. By simultaneously applying positive pressure at one site and negative pressure at the other site, injection is easier and material flows between the two sites instead of flowing away into undesirable areas.

Figure 1:
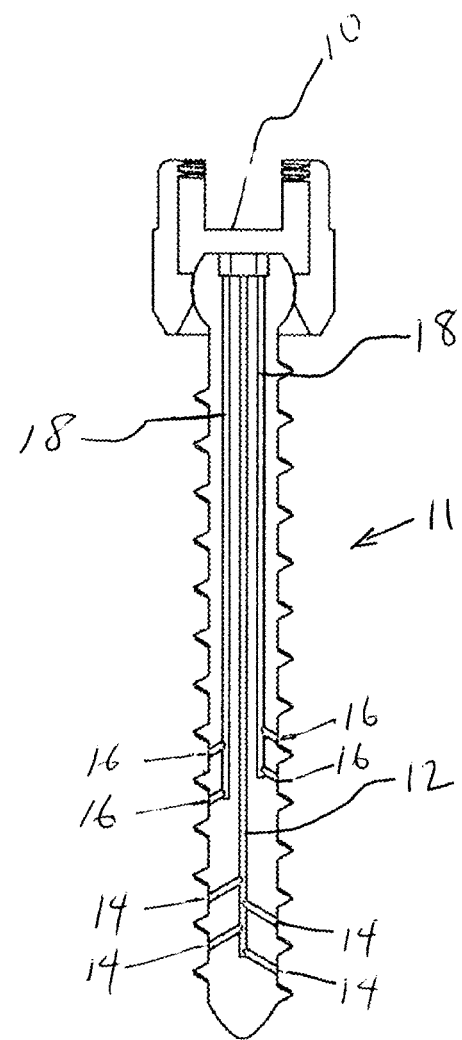
FIG. 1 is a cross-section of a screw showing a possible configuration of channels to allow flow of material delivered into the head of the screw through a central cannulation, out into the anatomical region through distal radial fenestrations near the tip, back into the screw through radial fenestrations more proximal to the head, and then back through radially offset cannulations and up the shaft toward the screw head.

The channels can be straight, parallel to each other and collinear with the long axis of the bone screw/anchor device. Referring to FIG. 1, material may be delivered into the head 10 of the multi-port screw 11 through a central cannulation 12, out into the anatomical region through distal radial fenestrations near the tip 14, back into the screw through radial fenestrations more proximal to the head 16, and then back through radially offset cannulations 18 and up the shaft toward the screw head 10.

Alternately one or both channels can be curved, non-parallel to each other and at an angle with the long axis of the bone screw/anchor device. Thus, the openings can be anywhere (and strategically placed) along the bone screw/anchor device. One channel can coincide with the center long axis of the bone screw/anchor device, or both channels can be away from the center long axis.

Figure 2:
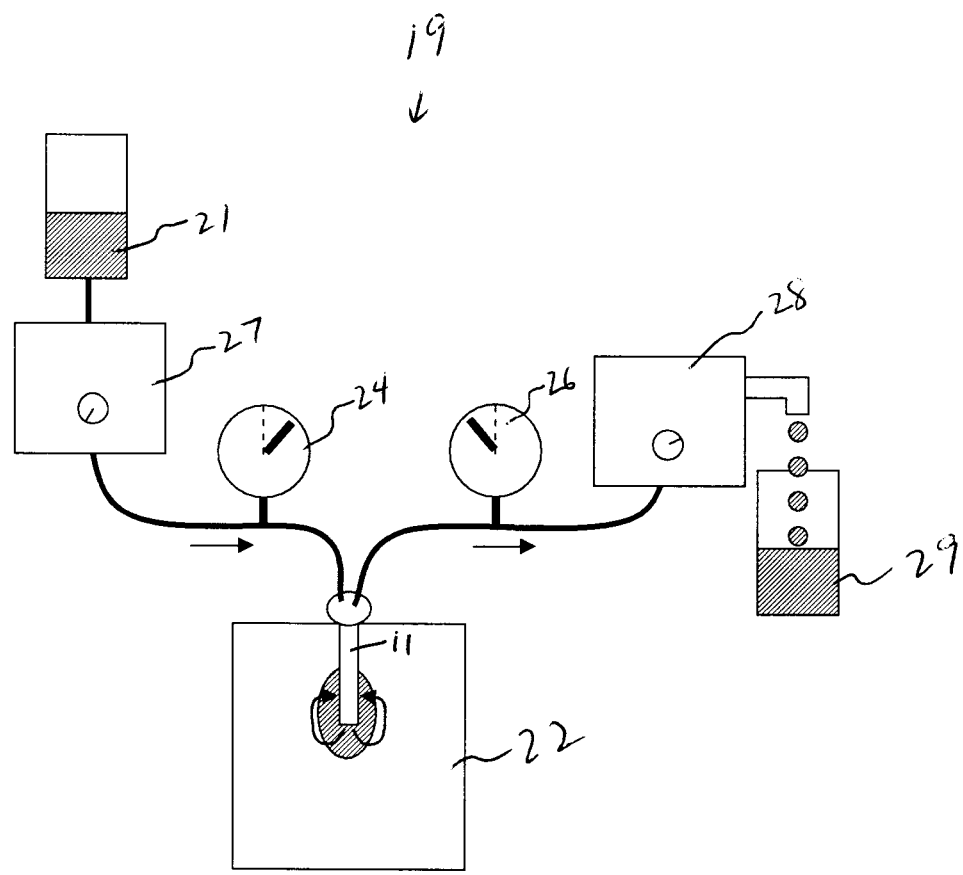
FIG. 2 is a possible configuration of a system for pumping injectate into the appropriate channel in the screw while simultaneously drawing the fluid out through the appropriate independent channel using a vacuum.

Referring to FIG. 2, the channels for ingoing and outgoing materials in the multi-port screw 11 that has been inserted in bone or other tissue 22 can be connected to and used with an external pressure-monitoring system 19, which can be used to control the rate and amount of the injected liquid 21. Pressure on both the positive pressure side 27 and the negative pressure side 28 are monitored with a positive-pressure-side gauge 24 and a negative-pressure-side gauge 26. Controllable valves on positive pressure side 27 and negative pressure side 28 can be controlled to adjust the flow in and out of the screw, either manually through dials or automatically through computerized control of the valves. Outflow of injectate and other waste (e.g., blood) is collected 29.

An alternative to using the controllable pressure system shown in FIG. 2 with a single multi-port screw is to use it with multiple cannulated needles (or a dual-channel cannula with strategically placed openings) placed into a bone screw/anchor device having a single cannula/tunnel (with or without fenestrations). The needles may be inserted parallel or at an angle relative to each other, to the same or different lengths, where one needle is used to inject/deliver material, and the second (additional) needle is used to simultaneously suction material (body fluid) out of the bone/anatomic region near the site to be injected. The pressure used to remove fluid (i.e. suction) may be adjusted to compensate for the rate of flow of the injected material (i.e. depending on the viscosity of the injectate, etc.).

It is also possible, although probably not as well-controlled, to connect syringes to each channel, manually compressing one syringe while distracting the other to create positive and negative pressures.

Figure 3:
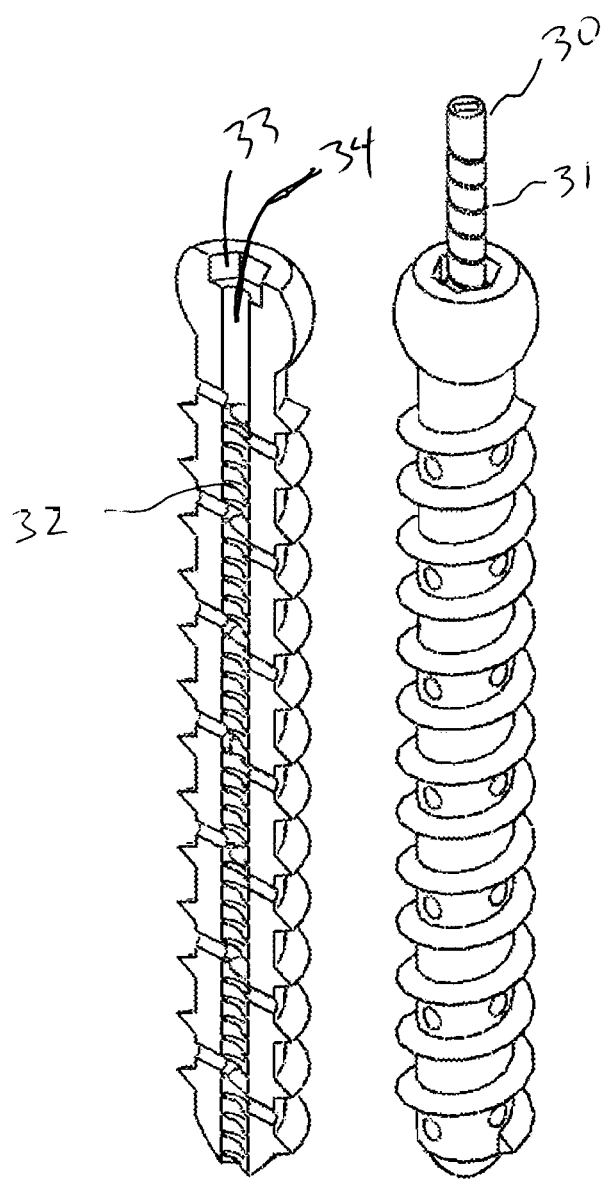
FIG. 3 demonstrates how a threaded cylinder can be inserted into a threaded channel to act as a plunger for creating positive pressure (if advanced) or suction (if withdrawn).

Another option for creating suction or positive pressure in a straight channel (either in a two-screw configuration as described below or in a single screw with multiple channels) is to use a "plunger" in the channel. Such a plunger could be either a straight cylinder or a threaded cylinder within a threaded channel, as is shown in FIG. 3. FIG. 3 shows both an axially cannulated and radially fenestrated screw as a cutaway view without plunger (left) and the whole screw with plunger 30 (right). After driving the screw into bone or tissue using a screwdriver that is suitable for the hex head socket in the screw head 33, material is injected into the central canal opening in the head of the screw 34. The plunger 30 is then inserted into the central canal. Threaded indentations 31 in the plunger mate with threads 32 in the wall of the cannulation, allowing the plunger to be advanced or withdrawn by rotating it clockwise or counterclockwise in the hole with a smaller screwdriver.

Figure 4:
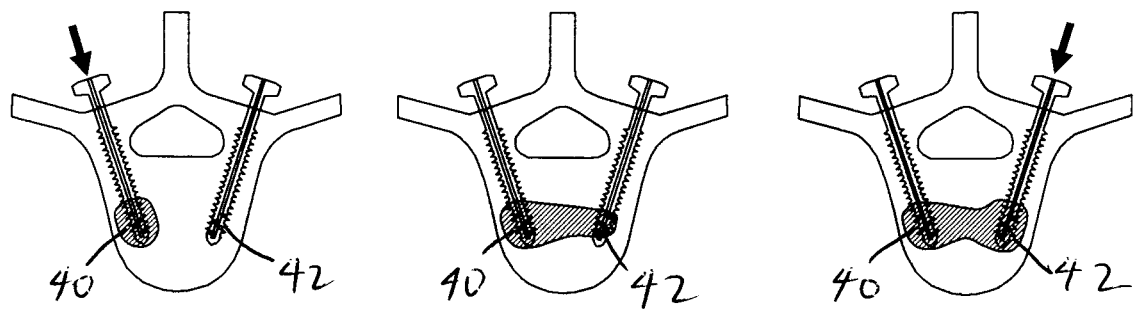
FIG. 4 demonstrates usage of two cannulated screws (cannulated with only a single channel) for intraoperative vertebroplasty or delivery of other material to the vertebral body.

An alternative embodiment involves the use of two cannulated (and possibly fenestrated) screws in the same piece of bone with tips in close proximity. As an example, two pedicle screws could be used during intraoperative vertebroplasty, where one screw is injecting under positive pressure while the other is withdrawing under negative pressure, allowing cement or material to flow between the screw tips. As with a single screw with multiple channels, this method prevents material from flowing outside the desired area. Referring to FIG. 4, injection begins (left image) with a single screw (left screw in this example), through which material flows and gathers near the fenestrations at the tip 40. Negative pressure is applied to the opposite screw (center image), causing material to flow toward the opposite screw tip 42 (right screw in this example) in a controlled way. If a more uniform distribution of material (right image) is desired, flow through the left screw can be halted or reversed and flow through the right screw reversed (that is, material injected from the right) to build up material near the right screw tip 42.

Figure 5:
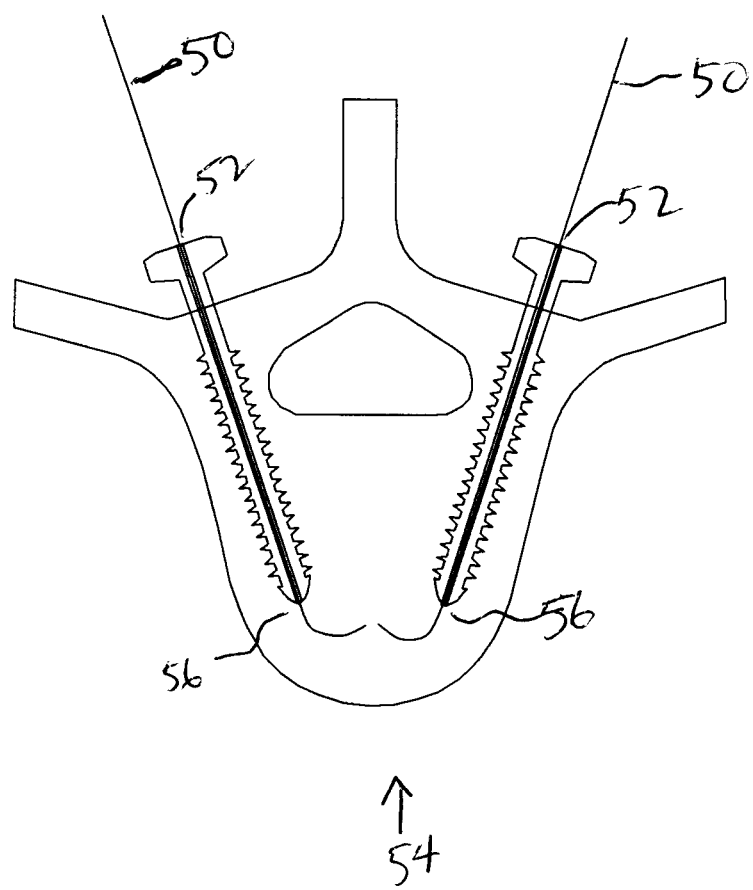
FIG. 5 demonstrates how pilot holes may be reamed by inserting wires through one or both cannulated screws if the material through which the injectate must flow (e.g., bone) is not porous enough and the two screw tips do not communicate.

Depending on the porosity of the bone or material between the screw tips, this two-screw technique may or may not require a pilot channel to be created so material can flow between screw tips. Referring to FIG. 5, to create a pilot hole, a reaming wire 50 may be passed through the cannulation 52 and into the bone or tissue 54. The reaming wire may be comprised of shape memory alloy such as Nitinol in a pre-coiled configuration that would allow it to angulate after exiting the tip of the screw 56 if a nonlinear pilot hole pathway is desired. Such wires could be forced into the cannulation and advanced through the straight channel, but would curl as they exited the tip.

It will be understood that implementations are not limited to the specific components disclosed herein, as virtually any components consistent with the intended operation of a method and/or system implementation for a phone system may be utilized. Accordingly, for example, although particular component examples may be disclosed, such components may comprise any shape, size, style, type, model, version, class, grade, measurement, concentration, material, weight, quantity, and/or the like consistent with the intended operation of a method and/or system implementation of embodiments of the present invention may be used. In addition, various other configurations may be used. For example, while a screw may be described as having a hex head or a flat head, any other types of screw heads may be used with affecting the operation of the invention.

In places where the description above refers to particular implementations of a caller identification system, it should be readily apparent that a number of modifications may be made without departing from the spirit thereof and that these implementations may be applied to other systems. The presently disclosed implementations are, therefore, to be considered in all respects as illustrative and not restrictive.

What is claimed is:

1. A device for insertion into bone or tissue comprising:
   a screw defining within and by a body of the screw a plurality of cannulations of differing lengths having distal ends that do not extend out through any external surface of the device, wherein said plurality of cannulations are each parallel to a central axis of said screw, and wherein said plurality of cannulations comprise at least a first cannulation, a second cannulation, and a third cannulation, said first, second, and third cannulations configured such that an injectate flows out through said first cannulation and flows in through said second and third cannulations; and
   one or more fenestrations coupled to each of said plurality of cannulations, wherein the one or more fenestrations coupled to the first cannulation are one or more radial fenestrations located near a distal end of the device that extend out from the first cannulation at any angle through a surface of a sidewall of the device, and the one or more fenestrations coupled to the second cannulation are one or more radial fenestrations that are more proximal than the one or more radial fenestrations of the first cannulation and that extend out from the second cannulation at any angle through a surface of a sidewall of the device.

2. The device of claim 1 wherein the one or more fenestrations coupled to the first cannulation are directly coupled to only the first cannulation and not the second cannulation and the one or more fenestrations coupled to the second cannulation are directly coupled to only the second cannulation and not the first cannulation.

3. The device of claim 1 wherein the one or more fenestrations coupled to each of said plurality of cannulations comprises at least two fenestrations coupled to each of said plurality of cannulations.

* * * * *